United States Patent
Blancke et al.

(10) Patent No.: US 10,512,732 B2
(45) Date of Patent: Dec. 24, 2019

(54) DRUG DELIVERY DEVICE WITH DOSE KNOB CLUTCH

(71) Applicant: SANOFI-AVENTIS DEUTSCHLAND GMBH, Frankfurt am Main (DE)

(72) Inventors: Stefan Blancke, Frankfurt am Main (DE); Axel Teucher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 90 days.

(21) Appl. No.: 15/036,525

(22) PCT Filed: Nov. 17, 2014

(86) PCT No.: PCT/EP2014/074710
§ 371 (c)(1),
(2) Date: May 13, 2016

(87) PCT Pub. No.: WO2015/074984
PCT Pub. Date: May 28, 2015

(65) Prior Publication Data
US 2016/0296711 A1   Oct. 13, 2016

Related U.S. Application Data

(60) Provisional application No. 61/907,472, filed on Nov. 22, 2013.

(30) Foreign Application Priority Data

Apr. 24, 2014   (EP) .................................. 14165753

(51) Int. Cl.
*A61M 5/00* (2006.01)
*A61M 5/315* (2006.01)
(Continued)

(52) U.S. Cl.
CPC .......... *A61M 5/31573* (2013.01); *A61M 5/24* (2013.01); *A61M 5/3146* (2013.01);
(Continued)

(58) Field of Classification Search
CPC .... A61M 2005/3126; A61M 2205/581; A61M 2205/582; A61M 5/24; A61M 5/31551;
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 1835774 | 9/2006 |
| CN | 101516421 | 8/2009 |

(Continued)

*Primary Examiner* — Rebecca E Eisenberg
(74) *Attorney, Agent, or Firm* — Fish & Richardson P.C.

(57) ABSTRACT

An assembly for a drug delivery device and an associated drug delivery device are provided. The device has a drug delivery device housing and a medicament contained in the drug delivery device housing. A clutch is established between the dose knob and the dial link to prevent inadvertent proximal axial movement of the lead screw away from the cartridge piston, which can lead to dosing inaccuracies.

22 Claims, 3 Drawing Sheets

(51) Int. Cl.
*A61M 5/24* (2006.01)
*A61M 5/31* (2006.01)
*A61M 5/32* (2006.01)

(52) U.S. Cl.
CPC ...... *A61M 5/3158* (2013.01); *A61M 5/31551* (2013.01); *A61M 5/31553* (2013.01); *A61M 5/31561* (2013.01); *A61M 5/31575* (2013.01); *A61M 5/3202* (2013.01); *A61M 5/3157* (2013.01); *A61M 5/31505* (2013.01); *A61M 5/31558* (2013.01); *A61M 5/31563* (2013.01); *A61M 5/31585* (2013.01); *A61M 2005/3126* (2013.01); *A61M 2205/581* (2013.01); *A61M 2205/582* (2013.01)

(58) Field of Classification Search
CPC .......... A61M 5/31553; A61M 5/31558; A61M 5/31561; A61M 5/31575; A61M 5/3158; A61M 5/31585; A61M 5/3202
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2006/0206057 A1* | 9/2006 | DeRuntz | A61M 5/31551 604/224 |
| 2009/0275916 A1 | 11/2009 | Harms et al. | |
| 2009/0318865 A1* | 12/2009 | Moller | A61M 5/31553 604/135 |

FOREIGN PATENT DOCUMENTS

| | | |
|---|---|---|
| CN | 101448536 | 1/2011 |
| EP | 0937471 | 8/1999 |
| EP | 0937476 | 8/1999 |
| JP | 2007-502146 | 2/2007 |
| JP | 2009-537196 | 10/2009 |
| WO | 99/38554 | 8/1999 |
| WO | 01/10484 | 2/2001 |
| WO | 2005/018721 | 3/2005 |
| WO | 2007/134954 | 11/2007 |
| WO | 2008/037801 | 4/2008 |

\* cited by examiner

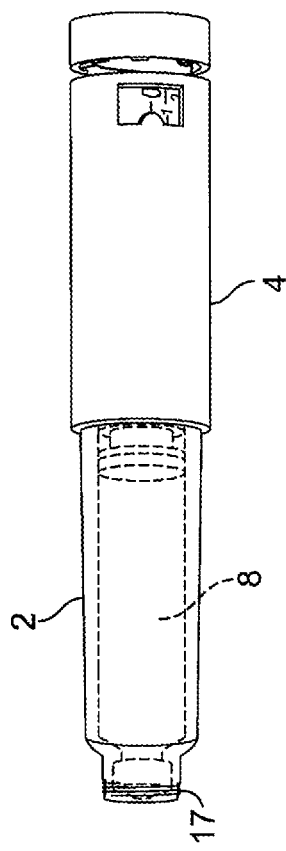
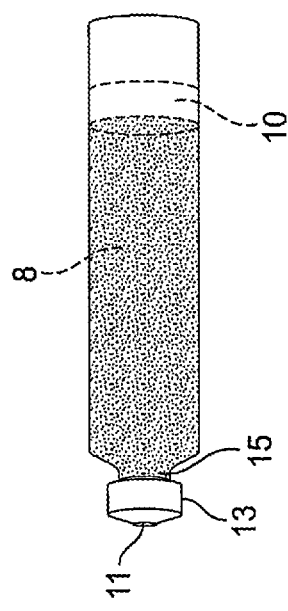
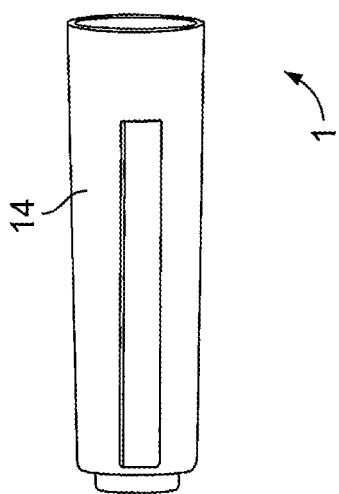
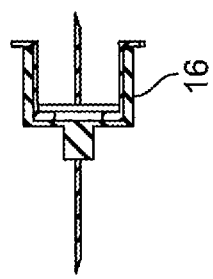
FIG. 1
FIG. 2

DRUG DELIVERY DEVICE WITH DOSE KNOB CLUTCH

CROSS REFERENCE TO RELATED APPLICATIONS

The present application is a U.S. National Phase Application pursuant to 35 U.S.C. § 371 of International Application No. PCT/EP2014/074710 filed Nov. 17, 2014, which claims priority to U.S. Provisional Patent Application No. 61/907,472 filed Nov. 22, 2013 and European Patent Application No. 14165753.6, filed Apr. 24, 2014. The entire disclosure contents of these applications are herewith incorporated by reference into the present application.

TECHNICAL FIELD

The present patent application is generally directed to drug delivery devices, such as injection devices as, for example, pen-type injection devices and to assemblies for drug delivery devices. Specifically the application is directed to dose setting and/or dose delivery mechanisms for such drug delivery devices. Such devices provide for self-administration of medicinal product from a multi-dose cartridge and permit a user to set the delivery dose. The present application may find application in both disposable and reusable type drug delivery devices. However, aspects of the disclosure may be equally applicable in other scenarios as well.

BACKGROUND

Pen type drug delivery devices have application where regular injection by persons without formal medical training occurs. This is increasingly common among patients having diabetes where self-treatment enables such patients to conduct effective management of their disease. Diabetes has been shown to cause certain problems. For example, people with diabetes can get high blood pressure, kidney disease, nerve damage, heart disease, and even in certain circumstances blindness. The damage caused by these problems may occur in patients whose blood sugar has been out of control for years. Keeping blood sugar under control, by way of effective insulin administration, is one method that can help prevent this damage from occurring.

In addition, people with diabetes can go into "diabetic coma" if their blood sugar is too high. They can also develop blood sugar that is too low (i.e, hypoglycemia) if they don't get enough food, or they exercise too much without adjusting insulin or food. Both diabetic coma and hypoglycemia can be very serious, and even fatal, if not treated quickly. Closely watching blood sugar, being aware of the early signs and symptoms of blood sugar that is too high or too low, and treating those conditions early can prevent these problems from becoming too serious.

Pen type drug delivery devices have been designed and developed to help patients suffering from diabetes and other disease states so as to prevent such problems from occurring. The circumstances identified above highlight a number of design considerations and criteria for drug delivery devices, especially those that may be used to treat diabetes. As just one example, one requirement is that the drug delivery device must be robust in construction. The drug delivery device must also be easy to use both in terms of the drug delivery device manipulation and understanding of the device's operation. Diabetics, for instance, have to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

Generally, pen type injection devices include a cartridge having a slidable piston and containing a multi-dose quantity of liquid medication. A lead screw extending from the dose setting mechanism of the injector pen is movable in a forward (i.e., distal direction) to advance the piston within the cartridge in such a manner as to dispense the contained medication from an outlet at the opposite cartridge end, typically through a needle that penetrates a stopper or septum at that opposite end. In disposable or prefilled pens where the cartridge is permanently sealed within the pen housing, after a pen has been utilized to exhaust the supply of medication within the cartridge, the entire pen is then discarded. In reusable pens, after a pen has been utilized to exhaust the supply of medication within the cartridge, the pen is disassembled to allow replacement of the spent cartridge with a fresh cartridge, and then the pen is reassembled for its subsequent use.

A number of pen type injection devices are commercially available and unfortunately a number of those devices suffer from one or more design flaws that may result in the improper use of the injection device or the delivery of an inaccurate dosing of the medicament. Inaccurate dose setting could lead to fatal results. Other design flaws allow the possibility that a counterfeiter can dissemble a disposable pen and insert bogus medicament cartridge. This pen is then reassembled and sold as new. Such design flaws may not be realized when a pen is first commercialized and may only become apparent after the injection device has been in commercial use by patients for an extended period of time. As such, there exists a need to evaluate existing pen designs to identify the design flaws and then take corrective action, which typically would include redesigning certain original mechanisms within the injection device.

One such pen injector lending itself to design improvements is described in WO 2005/018721. The following describes a number of such design flaws and presents corrective solutions which are, inter alia, suitable to eliminate these flaws.

SUMMARY

In most, if not all, pen injection type devices dose accuracy is significantly affected if the distal end of the lead screw, e.g. through the associated bearing, is not in continuous engagement with the proximal end or face of the cartridge piston, for example prior to the user setting a dose or before commencing dose delivery. Stated another way, in some dosing mechanism designs there is one or more flaws that allows the lead screw to move or otherwise translate off the piston proximally after a dose is injected and, for example, before a subsequent dose is set or before the delivery operation for delivering a set dose is commenced. In these cases the bearing is no longer in contact with the proximal end of the piston thus creating a gap or void space between the distal face of the bearing and the proximal face of the piston. When a next dose is set and delivered, the lead screw would necessarily traverse this unintended gap before contacting and moving the piston. Because there is no movement of the piston during this gap closure, and hence no expulsion of medicament from the cartridge, the actual dose delivered will be less than that set by an amount directly proportional to the size of the gap. Accordingly, it is of prime importance to prevent any unintended proximal movement of the lead screw between dose delivery and the setting of the next dose or between dose setting and before commencing the delivery of the set dose. Stated differently, the dosing mechanism should include structures to prevent, preferably any, proximal movement of the lead screw relative to the cartridge piston.

It is an object of the present disclosure to provide an assembly for a drug delivery device which facilitates provision of an improved drug delivery device and, particularly, to provide such an improved drug delivery device.

This object is achieved, inter alia, by the assembly in accordance with the independent claim but may also be achieved by different assemblies or systems as disclosed herein. Advantageous embodiments and refinements are subject-matter of the dependent claims and are also contained in the remaining specification.

According to an aspect, the present disclosure relates to an assembly for a drug delivery device. According to another aspect, the present disclosure relates to a drug delivery device comprising the assembly. Features disclosed herein above and below with respect to the assembly consequently also apply to the device and vice versa.

The assembly comprises a housing. Further components of the assembly such as components described above and below may be housed within the housing. The assembly further comprises a lead screw. The lead screw may have a distal end and a proximal end. The lead screw includes a threaded shaft. The assembly further comprises a drive nut. The drive nut is threadedly engaged with the lead screw, particularly with the threaded shaft thereof. The drive nut is screwable along the lead screw, particularly its threaded shaft. The drive nut may be screwable along the lead screw during dose setting. In other words, the drive nut may be screwed along the lead screw during a dose setting operation which is performed by a user of the assembly, such as when the assembly is prepared to perform a drug delivery operation after the dose setting operation has been completed. The assembly further comprises a dial link. The dial link is connected with the drive nut. Expediently, the dial link is axially movable and rotatably or rotationally fixed relative to the drive nut. Particularly, relative rotational movement between dial link and drive nut is preferably prevented. Axial relative movement between drive nut and dial link may be allowed. The dial link has a first clutch component. The assembly further comprises a dose knob. The dose knob may exhibit a user interface of the assembly. In other words, the dose knob may be arranged to be manipulated by the user for dose setting and/or dose delivery. The dose knob expediently comprises a second clutch component. The second clutch component may be cooperatively engagable with or may be cooperatively engaged with the first clutch component.

The first and second clutch components may be configured to interact to, preferably selectively, couple the dose knob and the dial link, for example rotationally, to one another, preferably at least when the two clutch components are engaged with each other. By means of the two clutch components the interaction between the dose knob and the dial link may be influenced in a positive way. For example, in a first state of the assembly, e.g. for setting a dose, the dose knob and the dial link may be rotationally coupled such that no relative rotational movement is permitted between these two components on account of the cooperative engagement of the first and second clutch components. Consequently, a rotational movement which is performed by the user and acts on the dose knob is, on account of the interacting clutch components, transferred to the dial link and, via the dial link, transferred to the drive nut, due to the rotational coupling of dial link and drive nut. On the other hand, the first and second clutch components may be configured such that, in a second state of the assembly different from the first state, e.g. not during dose setting, relative rotation between dose knob and dial link is permitted, preferably in two rotational directions or in only one rotational direction. Consequently, as relative rotation between dial link and dose knob is allowed in the second state when the dose knob is rotated relative to the drive nut rotation in the respective direction is not transferred to the dial link and, consequently, also not to the drive nut. Thus, it can be ensured that rotation of the dose knob does not have any effect on the drive nut when it is rotated in the direction in which relative rotation of dose knob and dial link is allowed. For example, it is possible that, when the dose knob is rotated in a rotational direction, the lead screw is moved proximally or distally relative to the housing, depending on the rotational direction, for example if the drive nut is axially fixed temporarily, e.g. due to a user handling the assembly in a wrong way which causes the drive nut to be stationary with the user simultaneously rotating the dose knob. A lead screw which moves into the proximal direction, i.e. the direction opposite to the one in which it should move during dose delivery, is usually undesirable as this usually affects dose accuracy negatively, for example because the lead screw is retracted from a piston within a cartridge. When the lead screw moves proximally unintentionally, even the size of the dose which will be actually delivered during the subsequent actuation of the assembly may be less than the dose which was set by the user, as the lead screw has to be moved distally by that distance which it has been moved proximally in order to re-assume the position it had before the (unintentional) proximal movement had been performed before the dispensing of the drug actually starts. A lead screw which unintentionally moves distally is also undesired usually, as this results in drug or medicament being expelled from the device without the intention of doing so. However, as compared to reduced dose accuracy unintended delivery is in most cases less critical. Accordingly, the assembly is preferably configured to at least prevent proximal movement of the lead screw, particularly in the second state of the assembly. For doing so, relative rotation between the dose knob and the dial link may be allowed in the second state of the assembly in that direction, which would cause proximal movement of the lead screw if that rotational movement were transferred to the dial link. Alternatively or additionally, the assembly is preferably configured to prevent distal movement of the lead screw, particularly in the second state of the assembly, by allowing relative rotation which would cause distal movement of the lead screw.

In summary, by means of the first and second clutch components which are cooperatively engagable, a considerably improved assembly for the drug delivery device may be provided.

In an embodiment, the assembly comprises a cartridge with a movable piston at one end and an outlet at the other end. The piston is engagable by the lead screw, particularly by a bearing foot thereof, to be advanced toward said outlet when the lead screw is moved, for example distally. Liquid drug or medicament may be contained in the cartridge. The drug or medicament may be expelled from the cartridge, if the piston is moved towards the outlet or in the distal direction.

In an embodiment, the first clutch component and the second clutch component are movable. The first clutch component and the second clutch component may be movable relative to each other, particularly in order to assume at least two different positions, preferably two different relative positions, a first position and a second position. In other words, the first clutch component and the second clutch component may be movable from a first position to a second position. The first and second position may be two different relative positions between the first clutch component and the second clutch component. The first position may be a rotatably fixed position, for example a position in which the dose knob and the dial link are rotatably or rotationally fixed to one another such that relative rotation between these two components is prevented. The second position may be a unidirectional rotation position or a bidirectional rotation position. In the unidirectional rotation position relative rotational movement in only one direction may be allowed between the dose knob and the dial link. Relative rotation in the second relative rotational direction may be prevented in this position. In the bidirectional rotation position relative rotation in both rotational directions may be allowed between the dose knob and the dial link.

Expediently, in the first position, the first and second clutch component cooperate to rotatably or rotationally fix the dose knob and the dial link relative to each other. In the second position, relative rotation between the dial link and the dose knob may be allowed in only one rotational direction or in both rotational directions. The first clutch component and the second clutch component may be in the first position during dose setting. The first clutch component and the second clutch component may be in the second position when the dose knob is subject to an external force, such as an axial force. An axial force may have to be exerted by the user for initiating dose delivery or during dose delivery, for example. However, such a force could also be exerted unintentionally, for example if the user has set a dose and plays with the dose knob, e.g. rotates it. In the second position, the second clutch component may cooperate with the first clutch component to prevent relative rotation in the one rotational direction in which no relative rotation is allowed or not cooperate at all with the first clutch component to allow rotation in both rotational directions.

In an embodiment, the dose knob is movable, preferably axially movable, relative to the dial link, particularly when the clutch components are in the first position. Consequently, the second clutch component may be movable relative to the first clutch component. Movement, e.g. axial movement, of the dose knob relative to the dial link, and particularly the associated movement of the second clutch component relative to the first clutch component, may cause movement of the second clutch component and the first clutch component from the first position to the second position.

In an embodiment, when in the second position, the first clutch component and the second clutch component may be axially offset from another, preferably in the distal direction. For example, the second clutch component may be arranged more distally with respect to the first clutch component in the second position as compared to the first position.

In an embodiment, during dose setting, the first clutch component and the second clutch component are in the first position. In this position, the dose knob and the dial link may be arranged to transfer a rotational movement of the dose knob, particularly relative to the housing, in a rotational dose setting direction to the drive nut via the dial link. The rotational dose setting direction may be that direction which increases the size of a set dose or prepares the device for a dose dispensing operation. In the first position, also, rotational movement in a dose cancelling direction which may be opposite to the rotational dose setting direction, may be transferred from the dose knob to the drive nut via the dial link. Consequently, doses may be increased and decreased by the user when the first and second clutch components are in the first position.

In an embodiment, in the second position, relative rotation between the dose knob and the dial link is allowed in a direction in and/or counter to the rotational dose setting direction.

Provided that, in the second position, the drive nut is axially fixed, and the dose knob were rotated counter to the rotational dose setting direction the drive nut would rotate counter to the dose setting direction if this rotation was transferred to the dial link and, due to this rotation, move the lead screw proximally. This is undesired and therefore, relative rotation in that particular direction between dose knob and drive nut is allowed.

Alternatively or additionally, in the second position, relative rotation between the dose knob and the dial link in the rotational dose setting direction may be allowed or prevented. If the relative rotation is allowed, no medicament will be expelled when the dose knob is rotated relative to the dial link in that direction. If relative rotation is prevented, this would result in the lead screw being displaced distally, thus potentially resulting in medicament being expelled from the device. If the user has, for example, moved the dose knob relative to the dial link in the distal direction, thus moving the clutch components into the second position, rotation in the rotational dose setting direction may cause small drops of medicament or drug to be dispensed from the device. Thus, the user may get an insight that the lead screw is indeed in contact with the movable piston in the cartridge and there is no need to worry about dose accuracy. Consequently, if a user has heard about the potential negative influence if a rotation counter to the rotational dose setting direction was transferred to the drive nut, his confidence in the device would be increased in this way as he can check that the lead screw is at its proper position because drug is dispensed. If no drug is dispensed, he could bring the lead screw into contact with the piston by according rotation of the dose knob until drug is expelled when the clutch components are in the second position.

In an embodiment, during dose delivery, the first clutch component and the second clutch component are in the second position. Consequently, during dose delivery the dose knob and the dial link may be rotationally selectively decoupled from another.

In an embodiment, the first clutch component and the second clutch component are biased into the first position by a spring. Thus, in the regular state of the assembly, the first and second clutch components are in the first position. The second position is assumed only if the spring force is overcome, for example by the user. Once the user force is removed, the components assume the first position again.

In an embodiment, the lead screw is rotatably or rotationally fixed during dose setting and/or dose delivery. Thus, rotation of the lead screw, particularly relative to the housing, may be prevented during dose setting and/or dose delivery. The lead screw may be movable, particularly axially movable, relative to the housing, for example in a distal direction. The lead screw may be axially guided within the housing, for example by lugs in a body part, such as a mid-body, engaging slots in the lead screw. The body part is expediently axially and rotationally fixed relative to the housing or formed unitarily with the housing. The lead screw may comprise a bearing foot connected to the distal end or forming the distal end.

In an embodiment, the assembly comprises a number sleeve. The number sleeve may be threadedly engaged with the housing, preferably to be screwable relative to the housing. The number sleeve and the dial link may be configured to assume two different axial arrangements. When the dial link and the number sleeve are in a first axial arrangement, the dial link may be rotatably or rotationally fixed with the number sleeve. Accordingly, the number sleeve is not rotatable with respect to the dial link in the first axial arrangement. When the number sleeve and the dial link are in the second axial arrangement, the number sleeve is preferably rotatable relative to the dial link. The respective coupling between the number sleeve and the dial link in the respective axial arrangement may be performed or provided by a clutch, which is expediently provided in addition to the first and second clutch components. The different axial arrangements may be achieved by relative axial movement between the dial link and the number sleeve. In the first axial arrangement, the first clutch component and the second clutch component may be in the first position. In the second axial arrangement the first clutch component and the second clutch component may be in the second position.

In an embodiment, the number sleeve and the dial link are biased from the second axial arrangement towards the first axial arrangement by a spring. The spring may be the spring which is provided to bias the first and second clutch components into the first position or a different spring.

In an embodiment, the assembly comprises an inner sleeve. The inner sleeve may be threadedly engaged with the number sleeve. The inner sleeve may be axially movable relative to the housing. The inner sleeve may be rotatably or rotationally fixed relative to the housing. Consequently, relative rotational movement between inner sleeve and housing may be prevented whereas axial movement may be allowed. The drive nut may be axially fixed to the inner sleeve. Consequently, drive nut and inner sleeve may translate in unison through the housing. Relative rotation between drive nut and inner sleeve may be allowed. This relative rotation may be used to provide a dose setting clicker of the assembly if corresponding clicker features on the drive nut and on the inner sleeve interact when the drive nut rotates relative to the inner sleeve.

In an embodiment, during dose setting, the dial link and the number sleeve are in the first axial arrangement. In this axial arrangement, a screwing motion of the dial link and the number sleeve relative to the housing screws the dial link and the number sleeve a first axial distance from a home position. The screwing motion of the dial link may screw the drive nut along the threaded shaft of the lead screw, particularly by a second axial distance that is different to the first axial distance.

In an embodiment, during dose delivery, the dial link and the number sleeve are in the second axial arrangement. In this arrangement, a screwing motion of the number sleeve relative to the housing back towards the home position may advance the inner sleeve without rotation in the distal direction to axially advance the drive nut and thereby the lead screw. The lead screw may advance the movable piston within the cartridge to dispense fluid from the cartridge outlet.

In an embodiment, the threading, e.g. the thread which defines the threaded engagement, between drive nut and lead screw is of a third lead, the threading of the inner sleeve to the number sleeve is of a second lead and the threading of the number sleeve to the housing is of a first lead. An arbitrary one of these leads may be different from an arbitrary one of the remaining leads. Preferably, any arbitrarily selected pair of these leads has two different leads. The first lead is preferably greater than the second lead and/or the third lead. The third lead is preferably smaller than the second lead. The sum of the second and third lead may equal the first lead. The specific leads of the threads which define the threaded engagement of the drive nut and the lead screw, the inner sleeve and the number sleeve or, where applicable, the number sleeve and the housing, facilitate that the drive nut and the inner sleeve are only displaced by a smaller extent axially than is the number sleeve.

In an embodiment, the dose knob has a distally facing alignment post. The alignment post may comprise the second clutch component.

In an embodiment, the dial link has a proximal projecting stem. The proximal projecting stem may have the first clutch component.

In an embodiment, the second clutch component comprises a plurality of, preferably inwardly facing, lugs. The lugs may be positioned radially or circumferentially around an inner portion of the alignment post.

In an embodiment, the first clutch component comprises a plurality of slots positioned radially or circumferentially around the stem. The slots may be configured to cooperatively engage the lugs in order to prevent or preventing relative rotation between the dose knob and the dial link. In an embodiment, the first clutch component comprises a plurality of angled clutch teeth. The clutch teeth may project radially outward from the stem. The clutch teeth may be positioned distally and/or adjacent to the lugs or the slots. Particularly, the clutch teeth may be positioned distally and adjacent to the lugs or the slots such that when the first and second clutch components are in the second position, the dose knob can be rotated relative to the dial link in only one direction. Rotation in the other direction can be prevented by cooperation of the lugs with steep sides of the angled clutch teeth. When the dose knob rotates relative to the dial link, less steep sides of the clutch teeth can cooperate with the lugs to allow relative rotation between dose knob and dial link.

Of course, the lugs, slots and/or teeth, respectively, could also be comprised by the other clutch component instead of the one described above.

A physical examination of the commercial pen injection device that is generally described in WO 2005/018721 shows that if a user pushes the dose knob in the distal direction and simultaneously rotates the dose knob in either direction (clockwise or counter clockwise) the lead screw is advanced in either the proximal and distal directions. Such a situation can develop as follows. The user begins to set a dose by rotating the dose knob causing the number sleeve to translate out proximally from the body. The user then grips the number sleeve preventing it from rotating and continues to rotate the dose knob while pushing the dose knob axially in the distal direction. This would cause the clutch to disengage from the dial link allowing relative rotation between dial link and number sleeve. Because the existing pen injection device is configured with the dose knob permanently attached to the dial link, rotation of dose knob necessarily rotates the dial link. Since the dial link is rotationally engaged with the drive nut trough the extending fingers, the drive nut also rotates. Rotation of the drive nut while preventing the number sleeve, and hence the inner sleeve, from moving will cause the drive nut to rotate in a fixed axial position. Since the drive nut is prevented from translating or screwing up/down along the lead screw, the lead screw, which is rotationally fixed by the mid-body, will be forced to translate axially relative to the threaded connection with the drive nut in either the distal or proximal direction depending on which way the dose knob is turned. If the lead screw translates distally it is possible to push the cartridge piston distally causing unwanted expulsion of medicament. If, however, the lead screw is caused to translate proximally then this will cause the bearing to disengage from the proximal face of the piston creating a gap that will lead to an inaccurate dose. To solve this problem, the concepts disclosed herein above and below could be applied to modify the original design of the dosing mechanism disclosed in WO 2005/018721 to prohibit this proximal motion of the lead screw.

Particularly, instead of having the dose knob and the stem of the dial link permanently connected, a second clutch mechanism is introduced between the stem of the dial link and the dose knob. This clutch mechanism may be additional to a clutch mechanism which couples the number sleeve and the dial link rotationally during dose setting and allows the number sleeve to rotate relative to the dial link during dose delivery. In the relaxed state (no external force on the dose knob), the second clutch needs to be closed, meaning no radial or rotational movement between dial link and dose knob is possible. The clutch could be held in the relaxed state via a biasing device, such as spring, washer, or the like component that is capable of exerting an axial biasing force. When the user applies a force on the dose knob (e.g., by pressing the dose knob in a distal direction) to dispense a dialed dose, the second clutch allows an axial movement of the dose knob relative to the dial link. This movement causes a change of the second clutch status or configuration. In the relaxed configuration the second clutch blocks any radial movement between the dose knob and the dial link and in the second configuration the second clutch changes to unidirectional blocking only or it does not block relative rotation at all. This means, in the second configuration, the dial link can rotate in one direction relative to the dose knob, but cannot rotate in the opposite direction. This unidirectional rotation is required in order be able to expel the medicament during dose delivery. Alternatively, relative rotation in both directions is allowed.

The pen type delivery device drug including the above described design improvement includes a housing, a lead screw having a threaded shaft which is rotatably fixed during dose setting and injecting, where the lead screw only moves axially in a distal direction relative to the housing during dose administration or delivery. The device also has a fluid container or cartridge defining a medicine-filled reservoir with a movable piston at one end and an outlet at the other end, where the piston is engaged by a bearing connected to the distal end of the lead screw. The piston is advanced toward the outlet or distal end of the cartridge when the lead screw is moved distally during dose administration.

A drive nut is threadedly engaged with the threads on the lead screw and can rotate and move proximally relative to the lead screw and housing during dose setting. A number sleeve is threadedly engaged with the housing and is screwed outwardly in the proximal direction relative to the housing during dose setting. A dial link is slidably and rotationally engaged with the drive nut and is axially movable and rotatably fixed relative to the drive nut. The dial link is rotatably fixed with the number sleeve through a clutch when the dial link and number sleeve are in a first axial arrangement and when in a second axial position the clutch, and hence the number sleeve, are disengaged from the dial link and the dial link becomes rotatable relative to the number sleeve. An inner sleeve is threadedly engaged with the number sleeve, were the inner sleeve is axially movable but rotatably fixed relative to the housing. During dose setting, the dial link and the number sleeve are in the first axial arrangement, whereby a screwing motion of the dose knob that is connected to the dial link and number sleeve relative to the housing screws the dial link and the number sleeve a first axial distance from a home position causing the number sleeve to extend in the proximal direction outwardly from the housing or body of the device. The screwing motion of the dial link screws the drive nut along the lead screw threaded shaft a second axial distance different than the first axial distance.

During dose dispensing, the dial link and the number sleeve element are in the second axial arrangement, whereby a screwing motion of the number sleeve relative to the housing back or inward toward the home position advances the inner sleeve without rotation in the distal direction to axially advance the drive nut and thereby the lead screw and the fluid container piston to dispense medicine from the outlet. The pen injector disclosed herein can be provided with a mechanical advantage that makes it easier for the user to push the dose knob during the dispensing of medication, which mechanical advantage can be very high and conveniently selected by the manufacturer during apparatus design. This mechanical advantage allows the number sleeve to travel a greater axial distance than the lead screw it advances, thus allowing for small doses to be delivered.

In the following text, a set of advantageous aspects is described. The aspects are numbered to facilitate referencing features of one aspect in other aspects. Features from the aspects are not only relevant in connection with the specific aspects they relate to but are also of relevance on their own.

1. A drug delivery device comprising:
   a housing;
   a lead screw having a distal end and a proximal end that is rotatably fixed during dose setting and dose delivery and axially movable in a distal direction relative to the housing, the lead screw including a threaded shaft and a bearing foot connected to the distal end;
   a cartridge with a movable piston at one end and an outlet at the other end, the piston engagable by the lead screw bearing foot to be advanced toward said outlet when the lead screw is moved distally;
   a drive nut threadedly engaged and screwable along the lead screw threaded shaft;
   a number sleeve threadedly engaged with the housing to be screwable relative to the housing;
   a dial link connected with the drive nut and axially movable and rotatably fixed relative to the drive nut, the dial link rotatably fixed with number sleeve when the dial link and number sleeve are in a first axial arrangement, the number sleeve rotatable relative to the dial link when the dial link and number sleeve are in a second axial arrangement, the dial link having a proximal projecting stem having a first clutch component;
   an inner sleeve threadedly engaged with the number sleeve, the inner sleeve axially movable and rotatably fixed relative to the housing;
   a spring biasing the number sleeve and dial link from the second axial arrangement toward the first axial arrangement; and a dose knob having a distally facing alignment post comprising a second clutch component cooperatively engaged with the first clutch component, where the first and second clutch components are movable from a rotatably fixed position to a unidirectional rotation position;

wherein the threading of number sleeve to the housing is of a first lead, the threading of the inner sleeve to the number sleeve is of a second lead, and the threading of the lead screw threaded shaft is of a third lead, and the first lead, the second lead and the third lead are not equal;

wherein during dose setting, the dial link and the number sleeve are in the first axial arrangement, whereby a screwing motion of dial link and number sleeve relative to the housing screws the dial link and the number sleeve a first axial distance from a home position, which screwing motion of dial link screws said drive nut along the lead screw threaded shaft a second axial distance that is different than the first axial distance; and wherein during dose delivery, the dial link and number sleeve are in said second axial arrangement, whereby a screwing motion of the number sleeve relative to the housing back toward the home position advances the inner sleeve without rotation in the distal direction to axially advance the drive nut that is axially fixed to the inner sleeve and thereby the lead screw and the movable piston to dispense fluid from the cartridge outlet.

2. The drug delivery device of aspect 1 where the first clutch component and the second clutch component are biased by the spring into the rotatably fixed position.

3. The drug delivery device of aspect 1 where the first clutch component comprises a plurality of inwardly facing lugs positioned radially around an inner portion of the alignment post.

4. The drug delivery device of aspect 3 where the second clutch component comprises a plurality of slots positioned radially around the stem and configured to cooperatively engage the lugs preventing relative rotation between the dose knob and dial link.

5. The drug delivery device of aspect 4 where the second clutch component further comprises a plurality of angled clutch teeth projecting radially outward from the stem and positioned distally and adjacent to the lugs such that when the when the first and second clutch components are in the unidirectional rotation position the dose knob can be rotated relative to the dial link in only one direction.

These as well as other advantages of the various aspects of our improved drug delivery device, and the manner of attaining them, will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 is an illustration of one embodiment of the present disclosure showing the assembled pen type medication dispensing apparatus where the cap has been removed to reveal the cartridge container or holder affixed to the dose setting mechanism;

FIG. 2 is a close up view of the cartridge container and the pen needle that is attached to the cartridge container for injection of the medicament;

Figure 3:
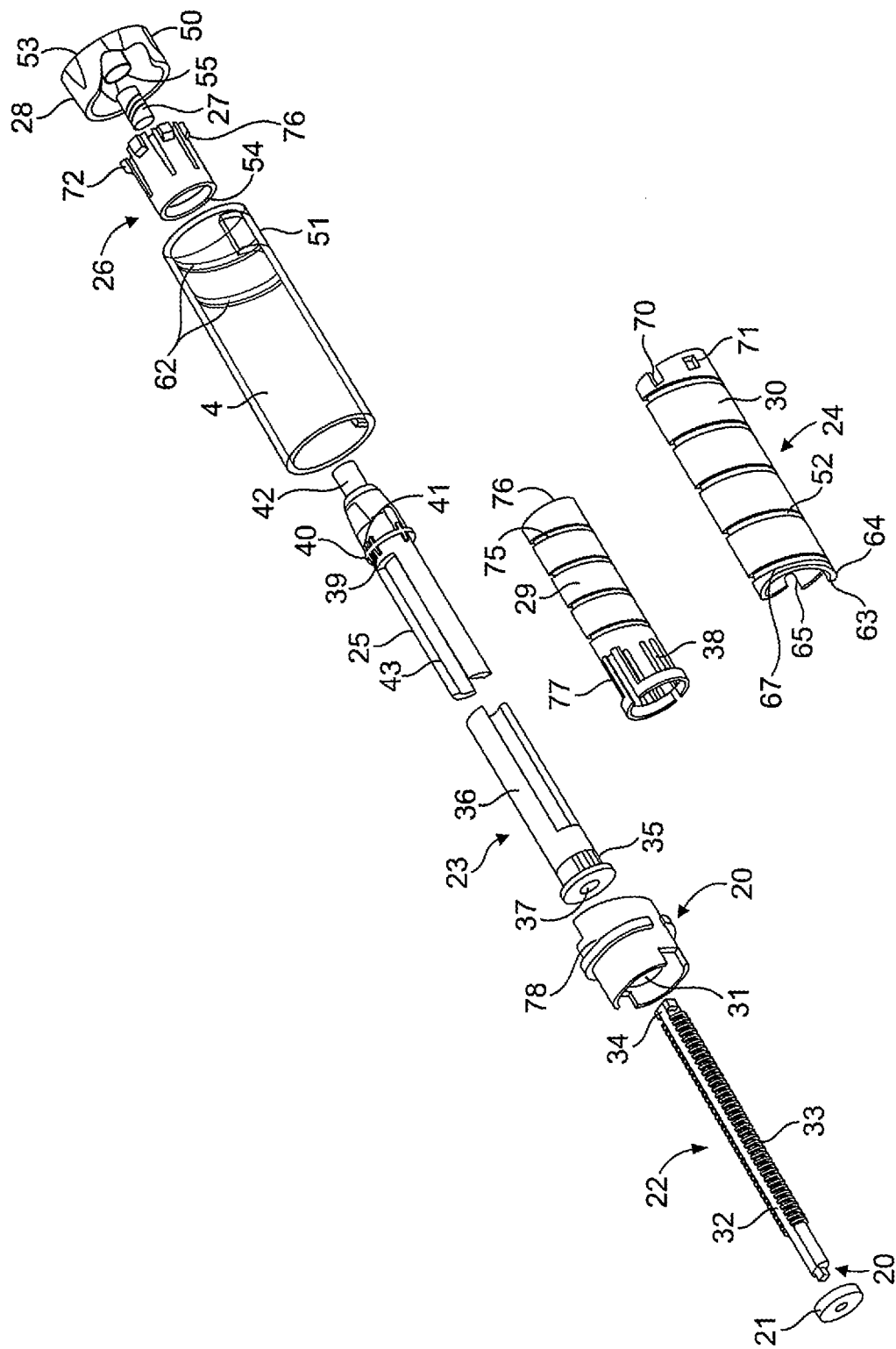
FIG. 3 is an exploded view of the embodiment from FIG. 1 showing each of the individual parts arranged relative to each other as they exist in the fully assembled device.

Corresponding reference characters indicate corresponding parts throughout the several views. Although the drawings represent embodiments of the present disclosure, the drawings are not necessarily to scale, and certain features may be exaggerated or omitted in some of the drawings in order to better illustrate and explain the present disclosure.

DETAILED DESCRIPTION

Referring first to FIGS. 1 to 3, there is shown a drug delivery device 1 as an injector pen, which pen has an elongated, substantially writing instrument-like form, although other forms are within the scope of the disclosure. In other words, the drug delivery device 1 may be a pen-type device. The drug delivery device 1 comprises a housing having a cartridge holder 2, and main (exterior) body or housing 4.

The drug delivery device 1 and the housing have a distal end and a proximal end. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the longitudinal axis or rotational axis of the device 1.

The proximal end of the cartridge holder 2 and the distal end of the main housing 4 are secured together by appropriate retaining features depending on whether the pen injector is designed as a reusable device or as a disposable device. In the latter case, the retaining feature would be permanent using the connection means described below. If the device is reusable, the retaining means or feature would be a screw type connection, a Luerlok or luer lock, snap fit, bayonet, or the like type or combination of fittings that allow the user to easily disassemble the device to replace the empty cartridge with a fresh new cartridge. In this illustrated arrangement, the cartridge holder 2 is secured within the proximal end of the main body 4.

A cartridge 8 from which a number of doses of a medicinal product may be dispensed is provided in the cartridge holder 2. Preferably, the cartridge contains a type of medicament that must be administered often, such as once or more times a day. One such medicament is insulin. A piston 10 shown in FIG. 2 is initially retained in the proximal end of the cartridge and as each injection is completed gradually moves distally to the empty cartridge position. A removable cap 14 is releasably retained connected to the main body 4 covering the cartridge holder 2. The dose setting mechanism of the drug delivery device illustrated in FIGS. 1 to 3 may be utilized as either for a disposable or reusable drug delivery device. Where the drug delivery device 1 comprises a disposable drug delivery device, the cartridge 8 cannot be removed from the device without destroying the device. In a disposable device, the proximal end of the cartridge holder 2 can be fixedly mounted or secured, via adhesives, ultrasonic welding or in another suitable manner, to the dose setting mechanism housing when the injector pen is assembled by the manufacturer. Alternatively, where the drug delivery device 1 comprises a reusable drug delivery device, the cartridge 8 is removable and may be removed from the device without destroying the device. In the drug delivery device 1 illustrated in FIGS. 1-3, the device is illustrated as a disposable drug delivery device. However, those of ordinary skill in the art will recognize that the dose setting mechanism could also be used on reusable drug delivery devices as well, while in the case of a reusable pen, wherein the cartridge holder may be reusable, such that the proximal end can be removably mounted or secured, for example via a threaded, bayonet, or snap fit connection, to a reusable dose setting mechanism having a resettable lead screw.

The removable or replaceable cap 14 is used to cover the cartridge holder 2 extending from the main housing 4. Preferably, the outer dimensions of the replaceable cap 14 are similar to or identical to the outer dimensions of the main housing 4 so as to provide an impression of a unitary whole part when the replaceable cap 14 is in position covering the cartridge holder 2. In use, the removable cap 14 is removed and a pen needle assembly 16 comprising a double-ended needle mounted in a hub may be screwed or pushed onto the distal end of the cartridge holder or alternatively may be snapped onto this distal end.

Cartridge 8 is of conventional design and defines a medicine-filled reservoir that is closed at its proximal end by the piston 10 that is axially slidably and sealably engaged with the cartridge interior wall to hold the fluid medication within the reservoir. The distal, outlet end of the cartridge reservoir is sealed by a septum 11 held by a cap 13 that is secured to a stepped-down diameter neck portion 15 of the cartridge. When pen needle assembly 16 is mounted on the distal end of the cartridge holder 2, the proximal point of injection needle 16 passes through a central opening in the distal end of the cartridge holder 2, an opening in cap 13, and penetrates cartridge septum 11 to provide a fluid flow outlet by which medicine within the cartridge reservoir can be dispensed from the distal needle tip during operations of injector pen 1. The fluid medicine cartridge shown and described above is illustrative and not intended to be limiting as other constructions may be employed within the scope of this disclosure.

Main body 4 of injector pen 1 houses an axially advanceable lead screw 22, a drive nut 23, an inner sleeve 29, a dial link 25, a number sleeve 24, a clutch 26, and a spring 27, such as a compression spring or biasing spring. A dose knob 28 is movably connected to the dial link 25 through a second clutch feature illustrated in FIG. 4 and described in more detail below. The dose knob 28 is used to set the dose and then to inject the set dose. Housing or main body 4 is formed from a lightweight material, such as injection molded plastic. The housing may be molded as a single, tubular piece for robustness. A window 51 in the housing near its proximal end can be filled with a magnifying lens that snaps fits to the housing and allows dosage indicating markings (not shown) on number sleeve 24 to be readily visible during use. Near the interior distal end of housing 4 is mounted a body part 20, e.g. a mid-body, that is formed with an a central opening having an inward facing anti-rotation mechanism formed from of a pair of diametrically opposed elements or tabs 31 having squared off inward ends that each slidably fit within longitudinal keyways 32 in lead screw 22. In alternate embodiments, features other than tabs and keyways, for instance a lead screw with flats that fits within a complementarily shaped hole in the collar, may be used to prevent rotation. Tabs 31 prevent lead screw 22 from rotating within housing 4 during pen use, but permit lead screw 22 to be shifted longitudinally, such as in the distal direction toward the cartridge. A snap fit or sonic welding connection of the mid-body to the, preferably tubular, housing 4 can be used to prevent axial and rotational relative motion of the mid-body to the housing.

Lead screw 22 is in the form of a screw that is axially translatable and rotatably fixed during dosing and injecting. The term "rotatably fixed" shall preferably mean that the lead screw 22 is prevented from rotation during dose setting and dose delivery. Lead screw 22 includes a shaft with a helical threading 33 along its length, which threading is interrupted by longitudinally extending keyways or grooves 32. A thread stop 34 shown at the proximal end of threading 33 is provided and is used in preventing the pen from being set by a user to deliver a dose of medicine larger than remains in cartridge 8. Other forms of stopping the screw motion may be substituted within the scope of the disclosure, for example, the threading at the proximal screw end could stop near the proximal end where it cannot be cammed in, and such solid screw with thread stop better ensures that the drive nut 23 will not be torqued off the lead screw during dose setting. The distal end of lead screw 22 includes an enlarged, disc-shaped foot or bearing 21 to distribute loading on the cartridge piston 10 that the bearing contacts and thereby directly engages during piston advancing. The separate bearing foot can be attached, such as with a snap fit 20 that may permit relative rotation, to the lead screw. Lead screw 22 is shown as being a one-piece plastic injection molding, but alternate materials of construction and multiple pieces are possible.

Drive nut 23 includes a cylindrical, tube-shaped body with flexible fingers 36 and clicker teeth 35. The distal region of the drive nut 23 is formed with an internal threading 37 that threadedly engages in a friction locking fashion or in a self-locking fashion the threading 33 on lead screw 22. Threadings 33 and 37 are shown as a double start threading but may be differently formed while still providing suitable friction locking capabilities, such as a single start threading or another multiple start threading. Drive nut 23 is located within inner sleeve 29 and is axially, but not rotationally fixed, to the inner sleeve. As drive nut 23 is rotated relative to inner sleeve 29 during dose setting, clicker teeth 35 engage in a ratchet fashion flexible arms 38 that project radially on the inside of inner sleeve 29. As the drive nut rotates the flexible arms ride over teeth 35 creating an audible clicking noise. The teeth are configured so that each click is equal to one dose volume being set. As few as one flexible clicker arm may be provided, but the use of three or four equally angularly spaced arms aids in centering drive nut 23 within the inner sleeve 29. The hollow interior of drive nut body 23 located proximally of threading 37 allows free passage of the proximal end of lead screw 22. The exterior surface of drive nut 23 is designed to cooperatively engage with dial link 25 so that the drive link is axially free and rotatably or rotationally fixed relative to drive nut 23. Thus, during use the dial link is axially movable relative to, but rotatably or rotationally locked with, the threaded drive nut. This connection is possible because of the cooperation of proximally extending fingers 36 on drive nut 23 and the distally extending fingers of dial link 25. These two sets of fingers 36, 43 move axially relative to each other but engage each other rotationally during dose setting when the dial link is rotated by turning dose knob 28, which is connected to the dial link through a second clutch feature described below. Drive nut 23 is shown as being a one-piece plastic injection molding, but other constructions are within the scope of the disclosure.

Figure 4:
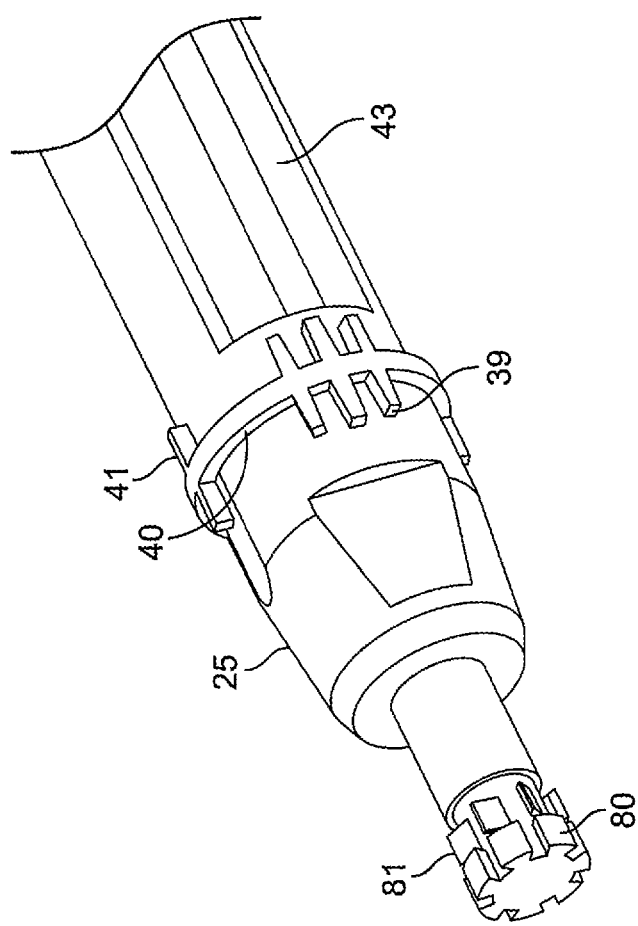
FIG. 4 is a perspective close-up view of one embodiment of the disclosure showing the second clutch mechanism between the dose knob and the dial link stem.
Figure 4:
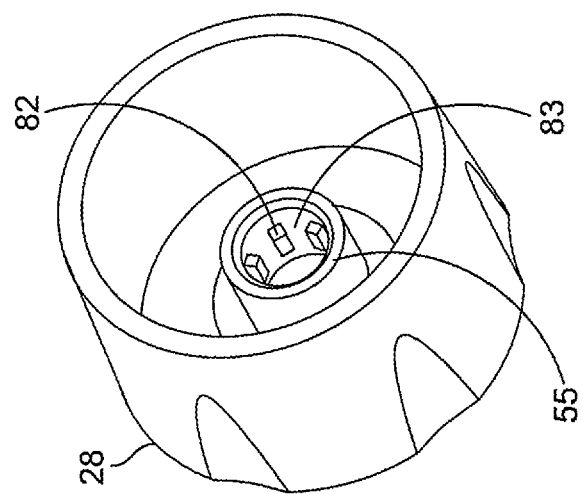

In the shown embodiment, dial link 25 is formed in one piece of an injection molded plastic and which fits within body 4. A flange 40 that rings a central region of the dial link body includes splines or teeth 39 that extend from the distal face of flange 40, and teeth 41 that extend from the proximal face of flange 40. A stepped-down portion of the proximal end of dial link 25 forms an axially and proximally extending stem 42. The distal end of the dial link body includes a pair of fingers 43 that fit with fingers 36 of the drive nut 23 to allow axial motion but not rotational motion of the drive nut 23 relative to the dial link 25, thereby rotationally locking the pieces together within the same annular space. Fingers 36 and 43 extend sufficiently axially to ensure they do not disengage during the setting of the maximum pen dose for injection. As illustrated in FIG. 4 the proximally extending dial link stem 42 contains structures 80 and 81 that constitute a first clutch component. At the most proximal end of stem 42 are a plurality of slots 80 positioned radially around the outer circumference of the stem. Immediately adjacent and positioned distally to slots 80 are a plurality of angled clutch teeth 81 projecting radially outward from the outer circumference of the stem. These two structures interact with and engage a second clutch component on dose knob 28 as described below.

An injection molded plastic dose knob 28 is provided with a proximal face, the dose knob having a distally facing and centrally located bearing collar and an alignment post 55. Dose knob skirt 50 distally extends from the radial periphery of the dose knob distal face to serve as a grip portion for a user during dose setting. Alignment post 55 is sized and configured to accept stem 42 of the of the dial link to form a second clutch of the dose or drug delivery device. Prior designs of this type of injection device required that the dial link stem and the dose knob alignment post 55 be permanently attached or fixed to each other, typically through an ultrasonically weld within the bearing collar during manufacturing assembly, so as to axially and rotatably fix together the dose knob 28 and dial link 25. As described above, this permanent fixation of the dial link and dose knob created a situation where a user could retract the lead screw bearing in a proximal direction creating a gap between the bearing and the proximal face of the cartridge piston. This would lead to dose inaccuracies during injection.

Alignment post 55 comprises the second part of the second clutch mechanism linking the stem to the dose knob. As illustrated in FIG. 4 the alignment post has an interior circumference 83 that contains a plurality of inwardly facing lugs 82 that are configured to engage slots 80 of the dial link stem when the second clutch is in a rotatably fixed position, meaning that the dose knob and the stem cannot rotate relative to each other. Stated another way, rotation of the dose knob by a user during dose setting (in either clockwise or counterclockwise direction) will necessarily cause the dial link to rotate in the same direction. In addition to the rotatably fixed position of the second clutch, the second clutch can move to a unidirectional rotation position when an axial force is applied to the dose knob in the distal direction, for example, if the user inadvertently pushes on the dose knob during setting of a dose. When the second clutch is in the unidirectional rotation position the dose knob can be rotated relative to the dial link in only one direction because of the angled configuration of the clutch teeth 81. When the dose knob is pushed or otherwise moved distally relative to the dial link the lugs 82 and slots 80 become disengaged and the lugs become engaged with the angled clutch teeth 81 to form a unidirectional coupling or ratchet that allows rotation in one direction, that being in the direction where the lugs can pass over the sloped or ramped angled surface of teeth 81. The ratchet teeth are preferably oriented to prevent rotation of the dose knob and dial link in a direction that would cause the lead screw to move proximally off of the cartridge piston. This unidirectional coupling created by the second clutch when in this second unidirectional rotation position would prevent a user from inadvertently rotating the dose knob during dose setting in a direction that would result in dosing accuracy. One or more biasing components, such as spring 27 or a different spring, can be used to bias the first clutch component and the second clutch component into the rotatably fixed position. As an alternative to the unidirectional coupling, in the unidirectional position, the angled clutch teeth 81 can be dispensed with, thus establishing a bidirectional position permitting relative rotation in both directions, i.e. clockwise and counterclockwise, when the dose knob has been displaced distally relative to the dial link.

Coaxially mounted around the dial link 25 is number sleeve 24. Number sleeve 24 has a cylindrical exterior surface 30 with a threading 52 formed as a helical groove that engages a corresponding threading 62 formed on the interior surface of body 4 to threadedly engage the number sleeve 24 to the pen housing. Threadings 52 and 62 are shown as a single start threading but may be differently formed. Threading 62 abuts an end 63 of threading 52 on the number sleeve 24 at the maximum pen dose, assuming the cartridge 8 is sufficiently full for such a maximum dose. A stop surface 64 on the distal end of the outer surface of the number sleeve 24 is positioned in slightly spaced apart relationship with a projecting stop at the zero dose position, and another stop surface is to be abutted by the stop if a user attempts to manually screw the screw element or number sleeve below a zero dose position. A hollow interior 65 of number sleeve 24 is defined by a cylindrical interior surface provided with a helical threading 67.

The outside diameter of number sleeve 24 is selected such that it can fit inside dose knob 28. The proximal end region of number sleeve 24 includes a number of notches 70 and corresponding windows 71 that are alternately spaced around the circumference. Number sleeve 24 includes around its exterior surface 30 suitable indicia of therapeutic dose size as visible through body opening 51. A clutch 26 fits within the open proximal end of number sleeve 24. Ears 72 on the clutch fit within notches 70 and assembly fingers 73 snap lock into windows 71 to axially and rotatably or rotationally lock the number sleeve 24 and the clutch 26 together during manufacturing assembly. A ring of axially extending teeth 54 on the clutch 26 formed in the interior surface of the flange cooperate with the dial link teeth 41 proximally facing on dial link 25. Disposed between the clutch 26 and the inside portion of the dose knob 28 is the spring that urges the clutch to engage teeth 41 on dial link 25. During injection, when a user manually applies a plunging force onto the proximal face of dose knob 28, the spring 27 is elastically compressed, thus disengaging the clutch 26 and the number sleeve 24 from the dial link 25. Flange teeth 41 on dial link and clutch teeth 54 mesh when spring 27 has biased the clutch and attached number sleeve to the dose knob and dial link. Dial link 25, and preferably dose knob 28, are not meshed with clutch 26 and number sleeve 24 when the spring has been sufficiently compressed during injecting. While a helically coiled metal wire spring is shown, other forms of commonly known biasing elements may be substituted.

Inner sleeve 29 is injection molded from plastic and includes a tubular body that fits into number sleeve hollow 65. The inner sleeve 29 has a helical threading 75 on its outer surface that engages internal threading 67 on inside surface of the number sleeve. Threadings 67 and 75 are shown as a single start threading, but may be differently formed. The most proximal portion of the end of inner sleeve 29, which end is partially helically shaped corresponding to the threading, is notched to form a partial ring of axially projecting teeth 76 that, when meshed with dial link distally facing teeth 39, serve to rotationally or rotatably lock together the dial link and the inner sleeve. Inner sleeve 29 is keyed to pen body 4 through the mid-body 20 that is axially and rotationally fixed to the body 4. The distal end of inner sleeve 29 has a pair of ridge-defined slots 77 on the periphery of the inner sleeve which axially, slidably receive the lugs 78 radially inwardly projecting from the mid-body 20. Openings molded into inner sleeve 29 define four resilient fingers 38 having radially inwardly projecting teeth that are axially oriented and shaped to project into a recess in the distal end of drive nut 23 that has radially projecting teeth or ridges 35 such that the inwardly projecting teeth click over, in either rotational direction, teeth 35 during dose setting. Fingers 38 with teeth cooperate with the recess on the drive nut 23 to hinder the nut from coming off the inner sleeve after being assembled thereto during manufacture.

To facilitate back-driving during dose delivery, the threaded connections of the number sleeve 24 and the body 4, and the number sleeve and the inner sleeve 29, are non-binding and provided by projecting 60° face angle threads that slide within correspondingly designed recessed grooves. With these threadings, it is preferred that the mechanical advantage is 3.4 or greater, and the screw lead of the drive member or drive nut is 0.108 inch.

The operation of the above described embodiment will now be explained. Pen 1 with a needle 16 attached should first be primed to remove any trap air in the cartridge 8 and to ensure the bearing 21 is in contact with the proximal end of the cartridge stopper or piston 10. In particular, typically while clutching the pen body 4 in one hand, a user manually grips dose knob skirt 50 and then begins to turn knob 28 relative to the body 4. At the zero dose arrangement, and as long as knob 28 is not also being plunged which is improper, knob can only be rotated in a dose increasing direction due to the number sleeve not being further movable distally. A user stops the rotating after a short amount of number sleeve travel that is associated with a small delivery volume, such as one or two units, which is indicated by markings visible through window 51. Then, and after removing cap 14 and any other needle cap present, and while pointing the needle tip upward, the user applies a plunging force on dose knob 28 to drive it distally until the number sleeve returns to the zero dose position, at which the number sleeve threading 52 has reached the distal end of the body threading 62, during which plunging action the piston 10 is shifted forward within cartridge 8. If a user sees that the piston movement has caused liquid to reach the needle distal tip, the priming process is complete. If no liquid is visible at needle tip, the priming steps are repeated as needed. After priming, pen 1 is ready to be used for an actual injection.

First, a user prepares the pen by setting the desired dose, as visible in window 51, by turning of knob 28. If the user dials up too large of a dose, and without expelling any medicine, the user can rotate down the dial by turning the knob in the opposite direction, all the way back to zero if desired. To set a dose, the knob is turned in a clockwise direction. Because the dose knob 28 and the dial link 25 are fixed rotationally when the second clutch is in the rotatably fixed position, the dial link 25 is rotated causing the distally facing fingers 43 to engage the proximally facing fingers 36 of the drive nut 23 to thereby turn the drive nut in same direction. Rotation of the drive nut causes the nut to rotate relative to the stationary lead screw 22 whereby the nut moves or climbs up the lead screw in the proximal direction. The drive nut 23 rotates relative to the inner sleeve 29 that is held rotationally fixed relative to the body 4 through the splined connection to the mid-body. Because drive nut 23 and inner sleeve 24 are axially fixed, proximal axial movement of the drive nut causes the inner sleeve to slide proximally relative to the mid-body 20. Because the clutch 26 is rotationally fixed with the dial link 25 the clutch 26 rotates causing the number sleeve to rotate and to spin out proximally away from body 4. Because the pitch or lead of the threads on the number sleeve are greater than the pitch or lead of the threads on the inner sleeve, the number sleeve and the dial link will translate a larger axial distance compared to the inner sleeve and the drive nut.

To inject the dose, after pen 1 is manipulated so the injection needle distal tip properly penetrates, for example, a user's skin, an axial, distal plunging force is applied to knob face 53 to force the dial link 25 axially in the distal direction towards the body 4, such as with a thumb or index finger of the hand which grasps the housing 4. Initially during injecting, the dose knob 28 moves slightly distally relative to the dial link 25 transforming the second clutch from the rotatably fixed position to the unidirectional or bidirectional rotation position. Once the stem 42 engages the inner distal face of the alignment post 55 the dose knob will cause the dial link to shift axially, which shifting motion compresses the biasing spring 27 to close the gap between the knob surface and the proximal end of the number sleeve. The biasing spring 27 is designed to compress prior to the number sleeve moving relative to the body 4. When dial link 25 shifts relative to number sleeve 24 to the axial arrangement of the drive nut 23, the clutch teeth 54 and dial link teeth 42 disengage to allow a back driving rotation of the number sleeve relative to the dial ink. During the axial movement of the dial link 25, drive nut 23 does not move axially or rotationally. When the number sleeve and clutch rotatably or rotationally uncouples from the dial link 25, as the dial link is continued to be axially plunged without rotation by the user by the plunging of knob 28, the number sleeve 24 screws into the body 4 as it spins relative to knob 28 and the dose markings on the number sleeve that indicate the amount still remaining to be injected is visible through window 51.

As it screws down, number sleeve causes inner sleeve 29 to in essence screw up the internal thread inside of the number sleeve threading as the inner sleeve advances distally a lesser distance than the number sleeve 24. The advancement of inner sleeve 29, due to the abutting or direct engagement with the distal end of the drive nut 23, advances the drive nut without rotation, which due to its threaded connection with the lead screw 22 advances the lead screw axially without rotation, which lead screw advancement shifts cartridge piston 10 to expel medication from the cartridge reservoir. The injection is completed when the number sleeve threading 52 has reached the distal end of the body 4, at which time pen 1 is once again arranged in the ready state or zero dose position.

Pen 1 can continue to be used to deliver any desired dose until the medicine remaining in the cartridge is insufficient for a proper dosing. This insufficiency is indicated to the user by the inability to fully set the desired dose due to drive nut threading 33 abutting thread stop 34 lead screw 22, at which time the drive nut and dial link cannot be rotated proximally any farther. When insufficient medicine remains, pen 1 may be disposed of and replaced with a similar but entirely new pen. Alternatively, a new cartridge may be provided and the pen may be reused.

The terms "medicament" or "medicinal product", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative; or an Exendin-4 derivative of the sequence des Pro36 Exendin-4(1-39)-Lys6-NH2 (AVE0010),
H-(Lys)6-des Pro36[Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38[Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5 des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

While this disclosure has been shown and described as having various designs, the present disclosure may be modified within the spirit and scope of this disclosure. For example, to deliver a fixed dose, the pen would preferably be modified such that the maximum that the dial could be screwed out to prepare the pen for injection would correspond to the fixed dose. Such a fixed dose pen could eliminate numerical dosage indicating marking, and instead provide user cues in the form of, for example, instructions and a graphical dosing indicator. This application is therefore intended to cover any variations, uses or adaptations of the disclosure using its general principles. Further, this application is intended to cover such departures from the present disclosure as come within known or customary practice in the art to which this disclosure pertains.

The invention claimed is:

1. An assembly for a drug delivery device comprising:
a housing;

a lead screw having a distal end and a proximal end, the lead screw including a threaded shaft;
a drive nut threadedly engaged with and screwable along the threaded shaft during dose setting;
a dial link, the dial link being axially movable and rotatably fixed relative to the drive nut, the dial link having a first clutch component;
a dose knob comprising a second clutch component cooperatively engagable with the first clutch component, where the dose knob has a user grip portion; and
in addition to the dose knob, a number sleeve movably retained in the housing.

2. The assembly of claim 1, where the first clutch component and the second clutch component are movable relative to each other to assume at least two different positions, a first position and a second position, wherein, in the first position, the first and second clutch component cooperate to rotatably fix the dose knob and the dial link relative to each other, and wherein, in the second position, relative rotation between the dial link and the dose knob is allowed in only one rotational direction or in both rotational directions.

3. The assembly of claim 2, where the dose knob is moveable relative to the dial link and movement of the dose knob relative to the dial link causes movement from the first position to the second position.

4. The assembly of claim 2, where, in the second position, the first clutch component and the second clutch component are axially offset from one another in a distal direction.

5. The assembly of claim 2, where, during dose setting, the first clutch component and the second clutch component are in the first position such that the dose knob and the dial link are arranged to transfer a rotational movement of the dose knob in a rotational dose setting direction to the drive nut via the dial link.

6. The assembly of claim 5, where, in the second position, relative rotation between the dose knob and the dial link is allowed in a direction counter to the rotational dose setting direction.

7. The assembly of claim 2, where, during dose delivery, the first clutch component and the second clutch component are in the second position.

8. The assembly of claim 2, where the first clutch component and the second clutch component are biased into the first position by a spring.

9. The assembly of claim 8, wherein the number sleeve is threadedly engaged with the housing to be screwable relative to the housing, the dial link being rotatably fixed with the number sleeve when the dial link and the number sleeve are in a first axial arrangement, the number sleeve being rotatable relative to the dial link when the dial link and the number sleeve are in a second axial arrangement, wherein, in the first axial arrangement, the first clutch component and the second clutch component are in the first position, and in the second axial arrangement, the first clutch component and the second clutch component are in the second position, and
wherein the number sleeve and the dial link are biased from the second axial arrangement towards the first axial arrangement by the spring.

10. The assembly of claim 2, wherein the number sleeve is threadedly engaged with the housing to be screwable relative to the housing, the dial link being rotatably fixed with the number sleeve when the dial link and the number sleeve are in a first axial arrangement, the number sleeve being rotatable relative to the dial link when the dial link and the number sleeve are in a second axial arrangement, wherein, in the first axial arrangement, the first clutch component and the second clutch component are in the first position, and in the second axial arrangement, the first clutch component and the second clutch component are in the second position.

11. The assembly of claim 10, comprising an inner sleeve threadedly engaged with the number sleeve, the inner sleeve being axially movable and rotatably fixed relative to the housing, wherein the drive nut is axially fixed to the inner sleeve,
wherein, during dose setting, the dial link and the number sleeve are in the first axial arrangement, whereby a screwing motion of dial link and number sleeve relative to the housing screws the dial link and the number sleeve a first axial distance from a home position, which screwing motion of the dial link screws said drive nut along the threaded shaft of the lead screw a second axial distance that is different than the first axial distance, and
wherein, during dose delivery, the dial link and the number sleeve are in said second axial arrangement, whereby a screwing motion of the number sleeve relative to the housing back toward the home position advances the inner sleeve without rotation in a distal direction to axially advance the drive nut and thereby the lead screw.

12. The assembly of claim 10, where the assembly comprises a clutch, which is provided in addition to the first and second clutch components, where the clutch is configured to rotatably fix the dial sleeve to the number sleeve when the dial link and the number sleeve are in the first axial arrangement, and to allow rotation of the number sleeve relative to the dial link when the dial link and the number sleeve are in the second axial arrangement.

13. The assembly of claim 1, where the lead screw is rotatably fixed during dose setting and dose delivery and axially movable in a distal direction relative to the housing.

14. The assembly of claim 1, where the dose knob has a distally facing alignment post, the alignment post comprising the second clutch component, wherein the second clutch component comprises a plurality of inwardly facing lugs positioned radially around an inner portion of the alignment post.

15. The assembly of claim 14, where the dial link has a proximal projecting stem having the first clutch component, wherein the first clutch component comprises a plurality of slots positioned radially around the stem and configured to cooperatively engage the lugs preventing relative rotation between the dose knob and the dial link.

16. The assembly of claim 15, where the first clutch component further comprises a plurality of angled clutch teeth projecting radially outward from the stem and positioned distally and adjacent to the slots.

17. The assembly of claim 1, where the dose knob exhibits a user interface of the assembly and is arranged to be manipulated by a user for dose setting and dose delivery.

18. The assembly of claim 1, where the user grip portion comprises a skirt distally extending from a radial periphery of the dose knob.

19. A drug delivery device comprising the assembly of claim 1 and a medicament.

20. The assembly of claim 1, wherein the number sleeve is threadedly engaged with the housing.

21. An assembly for a drug delivery device comprising:
a housing;
a lead screw having a distal end and a proximal end, the lead screw including a threaded shaft;
a drive nut threadedly engaged with and screwable along the threaded shaft during dose setting;

a dial link, the dial link being axially movable and rotatably fixed relative to the drive nut, the dial link having a first clutch component;

a dose knob comprising a second clutch component cooperatively engagable with the first clutch component, where the dose knob has a user grip portion, where the first clutch component and the second clutch component are movable relative to each other to assume at least two different positions, a first position and a second position, wherein, in the first position, the first and second clutch component cooperate to rotatably fix the dose knob and the dial link relative to each other, and wherein, in the second position, relative rotation between the dial link and the dose knob is allowed in only one rotational direction or in both rotational directions;

a number sleeve threadedly engaged with the housing to be screwable relative to the housing, the dial link being rotatably fixed with the number sleeve when the dial link and the number sleeve are in a first axial arrangement, the number sleeve being rotatable relative to the dial link when the dial link and the number sleeve are in a second axial arrangement, wherein, in the first axial arrangement, the first clutch component and the second clutch component are in the first position, and in the second axial arrangement, the first clutch component and the second clutch component are in the second position; and a clutch, which is provided in addition to the first and second clutch components, where the clutch is configured to perform the respective coupling between the number sleeve and the dial link in the first and second axial arrangements.

22. An assembly for a drug delivery device comprising:

a housing;

a lead screw having a distal end and a proximal end, the lead screw including a threaded shaft;

a drive nut threadedly engaged with and screwable along the threaded shaft during dose setting;

a dial link, the dial link being axially movable and rotatably fixed relative to the drive nut, the dial link having a first clutch component; and a dose knob comprising a second clutch component cooperatively engagable with the first clutch component, where the dose knob has a user grip portion, where the dose knob has a distally facing alignment post, the alignment post comprising the second clutch component, wherein the second clutch component comprises a plurality of inwardly facing lugs positioned radially around an inner portion of the alignment post.

* * * * *